(12) United States Patent
Dooney et al.

(10) Patent No.: US 11,653,909 B2
(45) Date of Patent: May 23, 2023

(54) SUTURE ANCHOR SYSTEMS WITH SPRING LOADED SUTURE ANCHORS

(71) Applicant: Arthrex, Inc., Naples, FL (US)

(72) Inventors: Thomas Dooney, Naples, FL (US); Reinhold Schmieding, Naples, FL (US)

(73) Assignee: ARTHREX, INC., Naples, FL (US)

( * ) Notice: Subject to any disclaimer, the term of this patent is extended or adjusted under 35 U.S.C. 154(b) by 463 days.

(21) Appl. No.: 16/810,021

(22) Filed: Mar. 5, 2020

(65) Prior Publication Data

US 2020/0197000 A1 Jun. 25, 2020

Related U.S. Application Data

(62) Division of application No. 15/656,281, filed on Jul. 21, 2017, now Pat. No. 10,646,215.

(51) Int. Cl.
*A61B 17/04* (2006.01)
*A61B 17/00* (2006.01)

(52) U.S. Cl.
CPC ...... *A61B 17/0401* (2013.01); *A61B 2017/00862* (2013.01); *A61B 2017/0403* (2013.01); *A61B 2017/044* (2013.01); *A61B 2017/0414* (2013.01); *A61B 2017/0417* (2013.01); *A61B 2017/0445* (2013.01); *A61B 2017/0448* (2013.01); *A61B 2017/0458* (2013.01)

(58) Field of Classification Search
CPC ..... A61B 17/04; A61B 17/0401; A61B 17/08; A61B 17/56; A61B 17/0469; A61B 2017/0414; A61B 2017/0445; A61B 2014/0403; A61B 2017/0417; A61B 2017/0409; A61B 2017/0458
See application file for complete search history.

(56) References Cited

U.S. PATENT DOCUMENTS

| | | | |
|---|---|---|---|
| 6,648,903 B1 | 11/2003 | Pierson, III | |
| 6,663,633 B1 | 12/2003 | Pierson, III | |
| 6,666,877 B2 | 12/2003 | Morgan et al. | |
| 8,764,798 B2 | 7/2014 | Housman | |
| 8,808,374 B2 | 8/2014 | Eggli | |
| 8,986,347 B2 | 3/2015 | Housman | |
| 9,271,826 B2 | 3/2016 | Eggli et al. | |
| 9,289,285 B2 | 3/2016 | Eggli | |
| 2013/0096611 A1* | 4/2013 | Sullivan | A61B 17/0485 606/232 |
| 2017/0049434 A1* | 2/2017 | Dooney, Jr. | A61B 17/0401 |

FOREIGN PATENT DOCUMENTS

WO 00/13601 A1 3/2000

* cited by examiner

*Primary Examiner* — Vi X Nguyen
(74) *Attorney, Agent, or Firm* — Carlson, Gaskey & Olds, P.C.

(57) ABSTRACT

An exemplary method includes fixating a first suture anchor in a first bone. The first suture anchor has a resilient member and a flexible strand attached to the resilient member. The flexible strand is passed to a second suture anchor, and tensioned. The second suture anchor is fixated in a second bone to secure the flexible strand to the second bone.

19 Claims, 5 Drawing Sheets

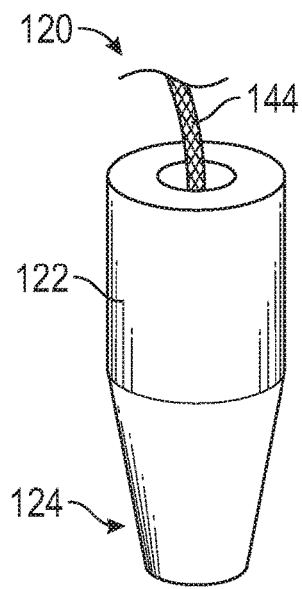 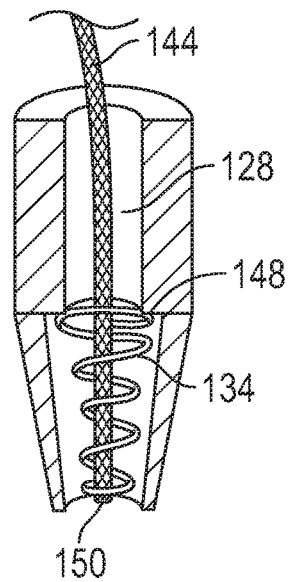 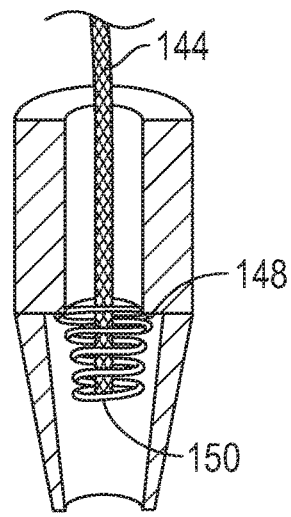
FIG. 3A    FIG. 3B    FIG. 3C
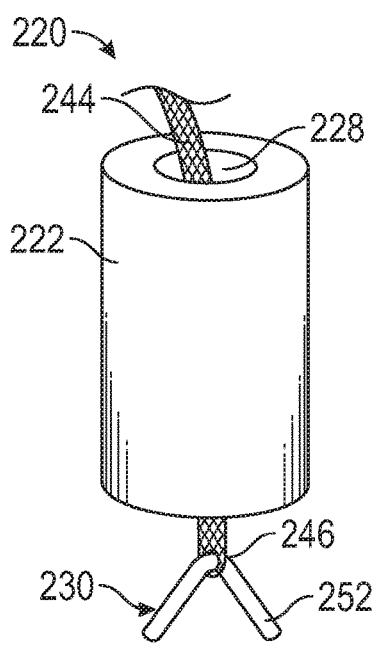 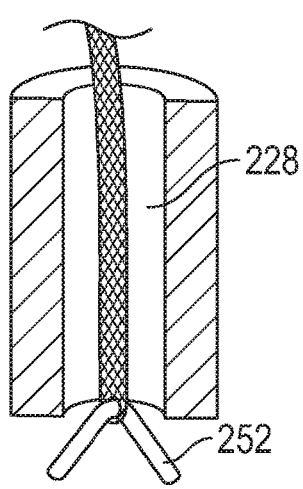 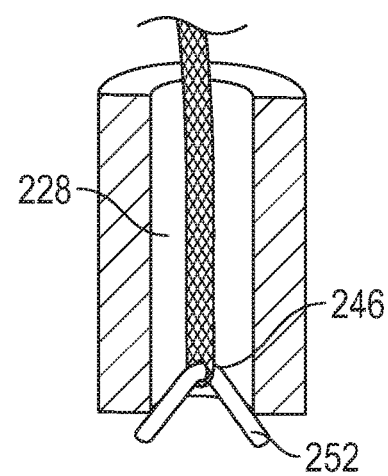
FIG. 4A    FIG. 4B    FIG. 4C

SUTURE ANCHOR SYSTEMS WITH SPRING LOADED SUTURE ANCHORS

CROSS-REFERENCE TO RELATED APPLICATIONS

This disclosure is a divisional of U.S. patent application Ser. No. 15/656,281 filed Jul. 21, 2017.

BACKGROUND

This disclosure relates to suture anchor systems for performing internal brace procedures. The suture anchor systems include spring loaded suture anchors.

Ligaments and tendons are soft collagenous tissues that play a significant role in musculoskeletal biomechanics. Ligaments connect bone to bone and tendons connect muscles to bone. Normal joint kinematics are achieved through balanced soft tissues that surround the articulating bones of a joint. An unstable joint occurs if there is significant disruption of the articulating bones or the surrounding soft tissues. This instability can cause pain, dysfunction, accelerated bone loss, soft tissue tears, premature arthritis, etc.

Suture anchors are used in many surgical procedures to attach suture to bone. A hole is drilled or punched in the bone, and a suture anchor is then inserted into the hole. A suture strand attached to the suture anchor is used to secure soft tissue to the bone.

SUMMARY

This disclosure details suture anchor systems and methods for improving biomechanical loading when repairing or reconstructing portions of a joint.

An exemplary suture anchor system includes a first suture anchor having a central axis, a distal end portion, a proximal end portion, and an internal passage extending along the central axis between the distal end portion and the proximal end portion. The resilient member is at least partially external to the internal passage, and a flexible strand is connected to the resilient member.

An exemplary method includes fixating a first suture anchor in a first bone. The first suture anchor has a resilient member and a flexible strand attached to the resilient member. The flexible strand is passed to a second suture anchor, and tensioned. The second suture anchor is fixated in a second bone to secure the flexible strand to the second bone.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

BRIEF DESCRIPTION OF THE DRAWINGS

FIGS. 3A-3C illustrate another embodiment of a spring loaded suture anchor.

FIGS. 4A-4C illustrate another embodiment of a spring loaded suture anchor.

DETAILED DESCRIPTION

This disclosure describes a suture anchor system and method of use for performing an internal brace procedure. An exemplary suture anchor system includes a first suture anchor having a central axis, a distal end portion, a proximal end portion, and an internal passage extending along the central axis between the distal end portion and the proximal end portion. A resilient member is at least partially external to the internal passage, and a flexible strand is connected to the resilient member. An exemplary method includes fixating a spring loaded suture anchor in a first bone, passing a flexible strand from the spring loaded suture anchor to a second suture anchor, and fixating the second suture anchor in a second bone.

The described suture anchors and surgical methods can be used in various internal brace tissue reconstruction procedures, including but not limited to, knee, ankle, and shoulder reconstructions. As used herein, the term "joint kinematics" generally refers to the manner in which the bones and surrounding soft tissue of a joint interact with one another during motion.

Figure 1:
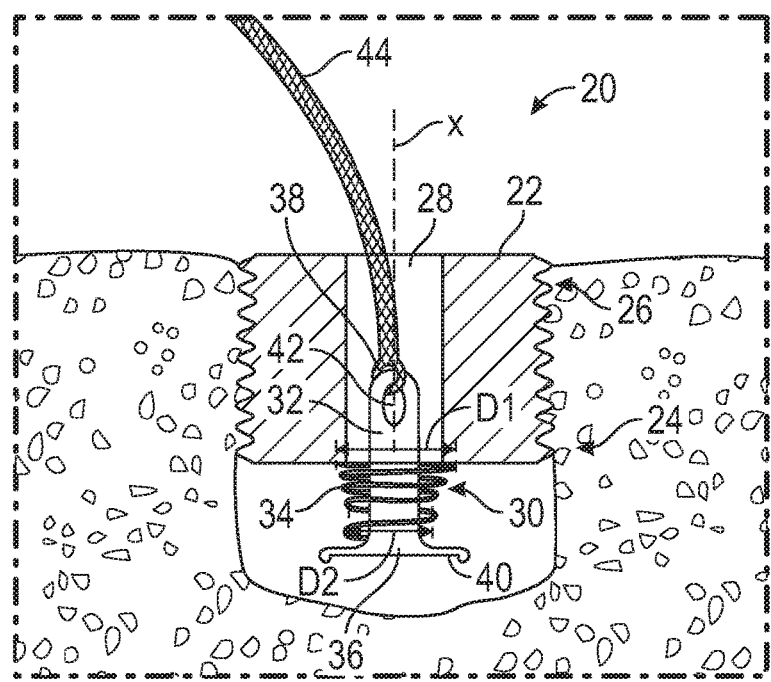
FIG. 1 illustrates a spring loaded suture anchor according to a first embodiment of this disclosure.

FIG. 1 illustrates a spring loaded suture anchor 20 according to an embodiment. The suture anchor 20 includes an anchor body 22 having a distal end portion 24 and a proximal end portion 26. The anchor body 22 has an internal passage 28 extending along a central axis X. The internal passage 28 extends from the proximal end portion 26 to the distal end portion 24. In some embodiments, an external surface of the anchor body 22 may be fully threaded or partially threaded. In other embodiments, the anchor body 22 may be a tap-in type anchor.

A resilient member 30 is disposed at the distal end portion 24 of the anchor body 22. In this embodiment, the resilient member 30 includes a post 32 and a spring 34. In an embodiment, the spring 34 is made from nitinol or another resilient biocompatible material. The spring 34 has an outer diameter D1 and an inner diameter D2. The outer diameter D1 is larger than a diameter of the internal passage 28, and thus the spring 34 cannot fit into the internal passage 28. The post 32 has a diameter that is smaller than the diameter of the internal passage 28 and the inner diameter D2 of the spring 34, and thus the post 32 fits into the internal passage 28. The post 32 has a distal end portion 36 and a proximal end portion 38. The distal end portion 36 of the post 32 includes a flared end portion 40. The flared end portion 40 has a diameter that is larger than the inner diameter D2 of the spring 34. In this embodiment, the proximal end portion 38 of the post 32 has an eyelet 42 for attaching a flexible strand, such as at least one strand of suture 44. The resilient member 30 can selectively provide dynamic tension on the suture 44.

Figures 2A, 2B, 2C:
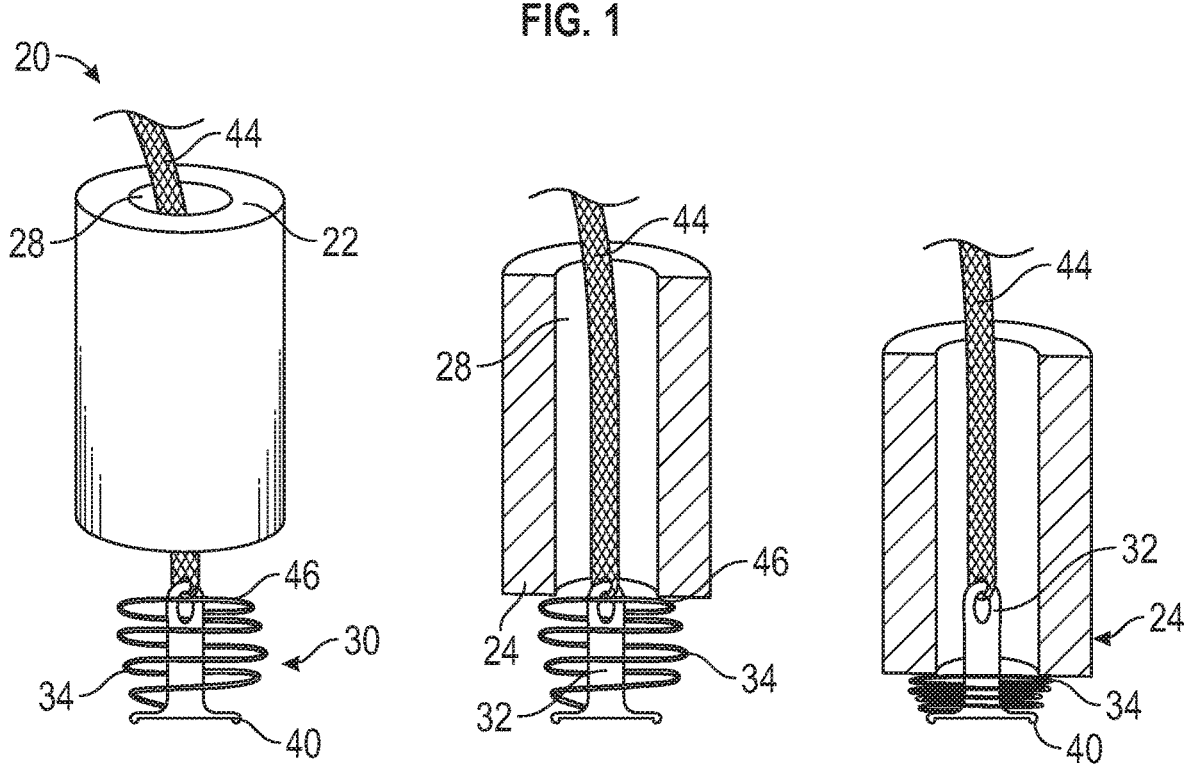
FIGS. 2A-2C illustrate another embodiment of a spring loaded suture anchor.

FIGS. 2A-2C illustrate an embodiment of a spring loaded suture anchor 20. In this embodiment, the spring 34 is entirely outside of the internal passage 28. As shown in FIG. 2A, the resilient member 30 is separate from the anchor body 22. As shown in FIGS. 2B and 2C, as tension on the suture 44 increases, the post 32 enters the internal passage 28, and a proximal end portion 46 of the spring 34 abuts the distal end portion 24 of the anchor body 22. As tension continues to increase, the spring 34 compresses, and is retained in a compressed state by the distal end portion 24 of the anchor body 22 and the flared end portion 40 of the post 32.

FIGS. 3A-3C illustrate another embodiment of a spring loaded suture anchor 120. In this embodiment, the internal passage 128 includes a shoulder 148, such that the internal passage 128 has a larger diameter distal to the shoulder 148 than the diameter proximal to the shoulder 148. In other words, the internal passage 128 includes a stepped design. In this embodiment, the spring 134 is inside the internal passage 128. The shoulder 148 maintains the spring 134 at the distal end portion 124 of the suture anchor 120. In some embodiments, the anchor body 122 is tapered at the distal end portion 124. In some embodiments, the spring 134 is tapered. The widest diameter of the spring 134 is greater than the diameter of the internal passage 128 proximal to the shoulder 148. The suture 144 may be secured to the spring 134 at a distal end portion 150. Positioning the spring 134 entirely inside of the internal passage 128 may prevent bone from growing in the spring 134.

FIGS. 4A-4C illustrate another embodiment of a spring loaded suture anchor 220. In this embodiment, the resilient member 230 includes a resiliently deformable tapered wedge 252. The deformable wedge 252 may be a compressible plastic material, bent stainless steel, titanium, or another resiliently deformable biocompatible material. The suture 244 may be attached to the deformable wedge 252 at a proximal end portion 246. The suture 244 may be attached to the deformable wedge 252 via an eyelet, however other ways of attaching suture 244 to the resilient member 230 are contemplated within the scope of this disclosure. As shown in FIGS. 4B and 4C, as tension is applied to the suture 244, the deformable wedge 252 compresses as it is pulled partially into the internal passage 228. The wedge 252 decompresses as tension on the suture 244 is released.

Figure 5A:
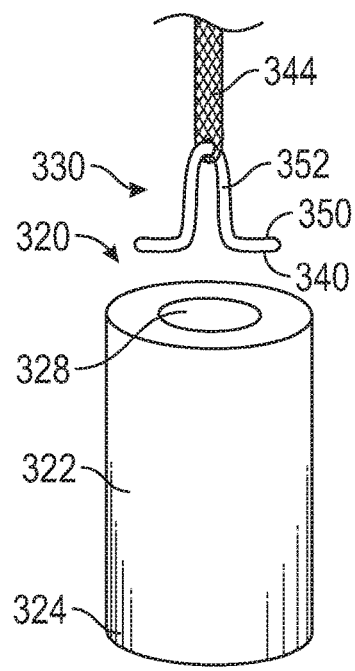
FIGS. 5A-5E illustrate another embodiment of a spring loaded suture anchor.
Figure 5B:
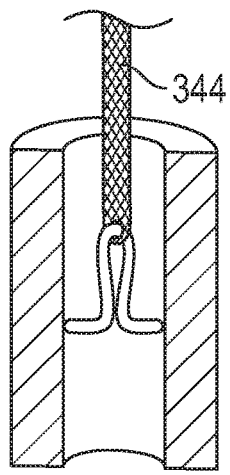
Figure 5C:
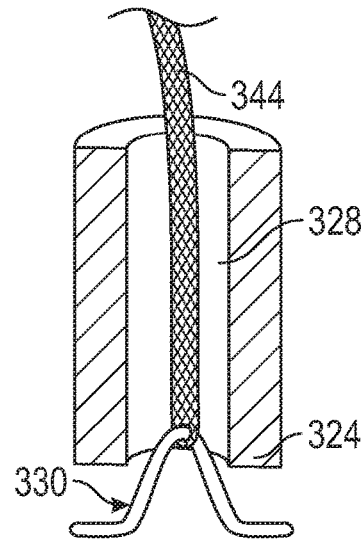
Figure 5D:
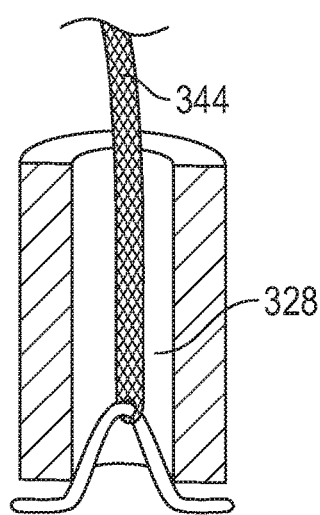
Figure 5E:
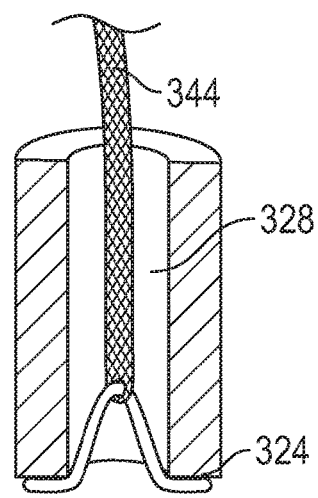

FIGS. 5A-5E illustrate yet another embodiment of a spring loaded suture anchor 320. In this embodiment, the resilient member 330 includes a resiliently deformable wedge 352 having a flared portion 340 at the distal end portion 350. The wedge 352 and suture 344 may be loaded after the anchor body 322 is secured, as shown in FIGS. 5A-5B. The deformable wedge 352 may be compressed and loaded through the internal passage 328. Once through the anchor body 322, the deformable wedge 352 expands at the distal end portion 324 of the anchor body 322, as shown in FIG. 5C. As tension is applied to the suture 344, the deformable wedge 352 compresses as it is pulled partially into the internal passage 328, as shown in FIGS. 5D-5E. The flared portion 340 at the distal end portion 350 of the wedge 352 retains the resilient member 330 at the distal end portion 324 of the anchor 320. When tension on the suture 344 is released, the wedge 352 decompresses.

Figure 6:
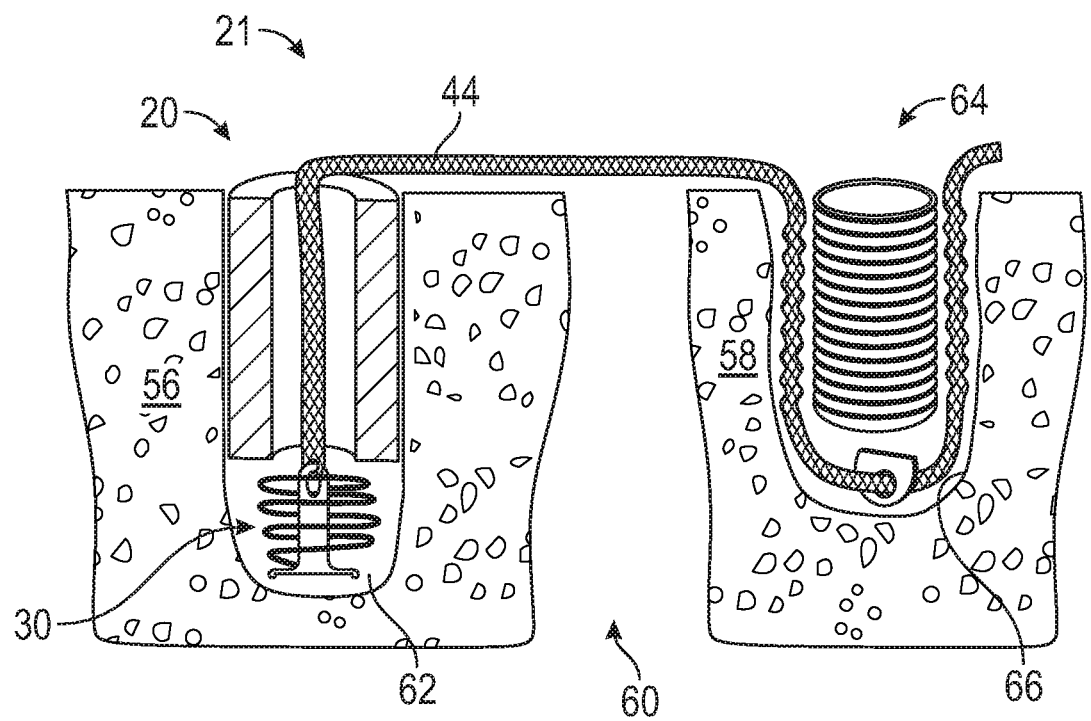
FIG. 6 schematically illustrates a method of using a spring loaded suture anchor as part of a suture anchor system for performing an internal brace procedure.

FIG. 6 schematically illustrates a suture anchor system 21 that includes a spring loaded suture anchor and surgical method of using the suture anchor system. The suture anchor system 21 includes a spring loaded suture anchor 20 and a non-spring-loaded suture anchor 64. A flexible strand 44 connects the spring loaded suture anchor 20 and the non-spring-loaded suture anchor 64. In an embodiment, the non-spring-loaded suture anchor 64 is a knotless suture anchor. The flexible strand 44 may be a suture strand, suture tape such as FiberTape®, a combination of suture strand and suture tape, a collagen tape, a suture with biological material, a tendon graft, or other suture material.

The suture anchor system 21 may be implanted within a first bone 56 and a second bone 58 of a joint 60 of the human musculoskeletal system. The joint 60 may be any joint of the musculoskeletal system of the human body. Tears of the muscles, tendons and/or ligaments at the joint 60 may require reconstruction. In some such reconstructions, a tendon, or a synthetic material, is employed as a graft, and is secured to the bones of the joint. In this way, the graft tendon functions as an internal brace ligament that supports the local tissue to help maintain normal joint kinematics. Using a spring loaded suture anchor 20 in such an internal brace procedure may help improve loading and joint kinematics.

For joint repair using a spring loaded suture anchor 20, the first bone 56 is prepared by drilling or punching a hole 62. A spring loaded suture anchor 20 is inserted into the hole 62 in the first bone 56. A flexible strand, such as suture 44 is fed from the spring loaded suture anchor 20 to a non-spring-loaded suture anchor 64. In an embodiment, the suture 44 may be fed through an eyelet or other capture device of the non-spring-loaded suture anchor. The second bone 58 is prepared by drilling or punching a second hole 66. The non-spring-loaded suture anchor 64 is inserted into the hole 66 in the second bone 58. In an embodiment, the suture 44 is tensioned such that the resilient member 30 of the spring loaded suture anchor 20 is compressed. In some embodiments, the suture 44 is tensioned prior to inserting the non-spring-loaded suture anchor 64 in the second bone 58. The tension on the suture depends on the application, and should be similar to the tension of the native ligament that is being repaired.

Known internal brace constructs have a static rigid suture between two bones, and when forces are applied between the two rigid anchors, the suture goes from slack to tight immediately. This rigid configuration may result in bone or construct damage, and the suture may not be able to regain its initial tension. The method of repairing a joint 60 using a spring loaded suture anchor 20 in a first bone 56 and a non-spring-loaded suture anchor 64 in a second bone 58 allows for variable tension on the suture 44. For example, if the bones shift, the spring loaded suture anchor 20 acts as a shock absorber, providing improved biomechanical loading. This configuration also allows for the suture 44 to be implanted under constant tension, and allows the repaired joint to act more like the native ligament.

Figure 7:
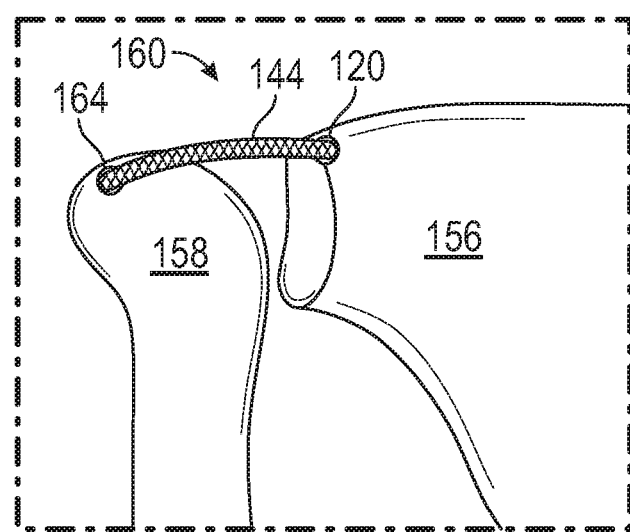
FIG. 7 illustrates an example method of using a spring loaded suture anchor for shoulder repair.
Figure 8:
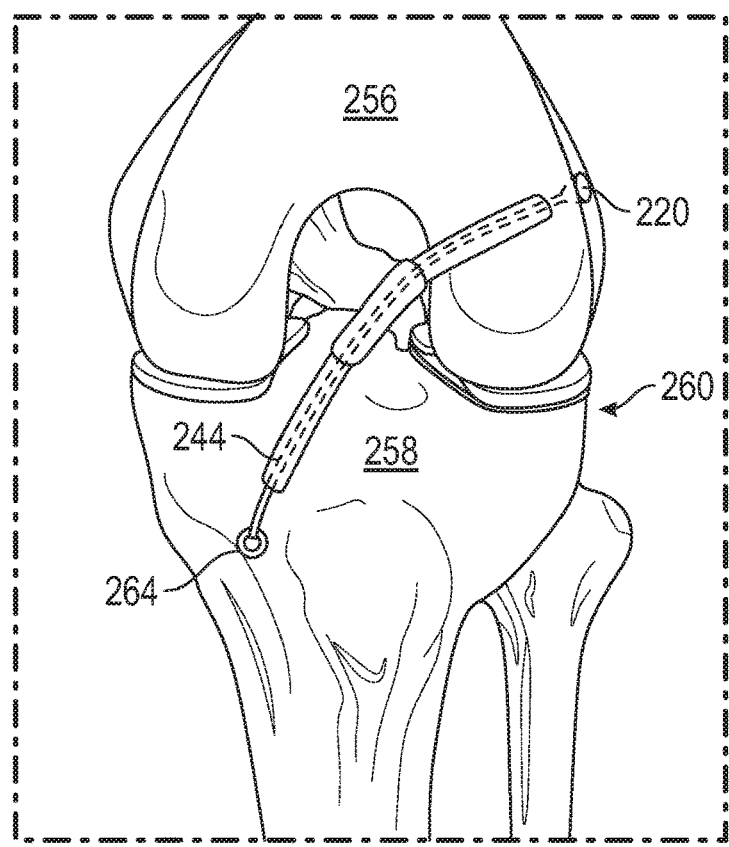
FIG. 8 illustrates an example method of using a spring loaded suture anchor for knee repair.
Figure 9:
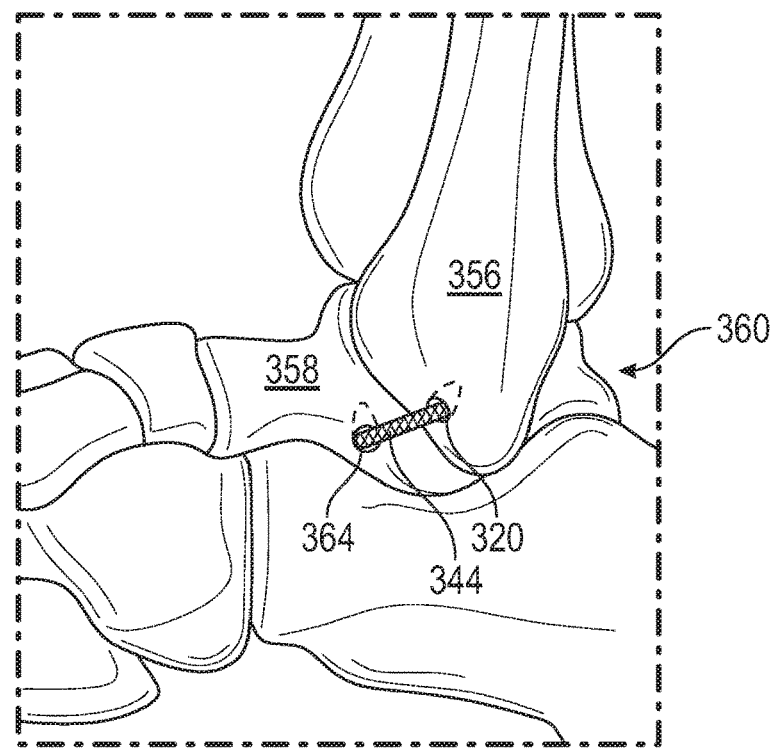
FIG. 9 illustrates an example method of using a spring loaded suture anchor for ankle repair.

FIGS. 7-9 illustrate exemplary joint repair applications for employing the use of a spring loaded suture anchor system. In a first embodiment, the joint 160 is a human shoulder, as shown in FIG. 7, that includes a first bone 156 (e.g., a scapula) and a second bone 158 (e.g., a humerus). The joint 160 may become unstable if there is significant disruption of the articulating bones, the superior capsular ligament, or surrounding muscles, tendons, and/or ligaments, such as a rotator cuff tear. One option for reconstruction of such a tear is to internally brace or support the rotator cuff repair so that the tendon need not function as both a tendon and ligament, thus improving longevity of the rotator cuff repair and improving the joint kinematics and function of the joint 160. In an example, a spring loaded suture anchor 120 is secured in the scapula 156, and a non-spring-loaded suture anchor 164 is secured in the humerus 158, with a graft or other flexible strand 144 between the anchors 120, 164. In another example, the spring loaded suture anchor 120 is secured in the humerus 158, and the non-spring-loaded suture anchor 164 is secured in the scapula 156. The use of a spring loaded anchor 120 improves joint kinematics by allowing variable tension and acting as a shock absorber.

In another embodiment, the joint 260 is a knee joint, as shown in FIG. 8. In this example, the first bone 256 is a femur, and the second bone 258 is a tibia. A spring loaded suture anchor 220 is secured in one of the first and second bones 256, 258, and a non-spring-loaded suture anchor 264 is secured in the other of the first and second bones 256, 258, with a graft or other flexible strand 244 between the anchors 220, 264.

In another embodiment, the joint 360 is an ankle joint, as shown in FIG. 9. This example reinforces or replaces an anterior talofibular ligament (ATFL). In this example, the first bone 356 is a fibula, and the second bone 358 is a talus. A spring loaded suture anchor 320 is secured in one of the first and second bones 356, 358, and a non-spring-loaded suture anchor 364 is secured in the other of the first and second bones 356, 358, with a graft or other flexible strand 344 between the anchors 320, 364.

Although schematically depicted, the method of FIGS. 6-9 may be performed as an arthroscopic procedure by working through various arthroscopic portals. Alternatively, the exemplary method could be performed as an open procedure.

The spring loaded suture anchor system of this disclosure is designed to improve joint kinematics for internal brace procedures. Known internal brace constructs have a static, rigid strand between two bones, and when forces are applied between the two bones, the strand goes from slack to tight immediately. Such a static, rigid structure may not be able to regain its initial tension, and could result in bone or construct damage. The spring loaded suture anchor system provides a shock absorbing element, allowing the construct to regain its initial tension after forces are applied between the two bones. The spring loaded suture anchor system also allows the suture to be implanted under tension.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical method, comprising:
    fixating a first suture anchor in a first bone, the first suture anchor having a resilient member and a flexible strand attached to the resilient member, wherein the resilient member includes a spring;
    passing the flexible strand from the first suture anchor through a portion of a second suture anchor;
    tensioning the flexible strand; and
    fixating the second suture anchor in a second bone to secure the flexible strand to the second bone; wherein the first and second bones are pre-drilled prior to fixating the first and second suture anchors.

2. The surgical method of claim 1, wherein the tensioning of the flexible strand compresses the resilient member.

3. The surgical method of claim 1, wherein the first and second bones are bones in a shoulder, knee, or ankle joint.

4. The surgical method of claim 1, wherein the second suture anchor is configured differently than the first suture anchor.

5. The surgical method of claim 1, wherein the second suture anchor is a knotless anchor.

6. The surgical method of claim 1, wherein the first anchor is a threaded anchor.

7. The surgical method of claim 1, wherein the passing the flexible strand comprises feeding the flexible strand through an eyelet of the second suture anchor.

8. The surgical method of claim 1, wherein the fixating the first suture anchor comprises drilling or punching a first hole in the first bone.

9. The surgical method of claim 8, wherein the fixating the second suture anchor comprises drilling or punching a second hole in the second bone.

10. The surgical method of claim 1, wherein the method is performed as an arthroscopic procedure.

11. A surgical method, comprising:
    fixating a first suture anchor in a first bone, the first suture anchor having a resilient member and a flexible strand attached to the resilient member;
    passing the flexible strand from the first suture anchor through a portion of a second suture anchor:
    tensioning the flexible strand; and
    fixating the second suture anchor in a second bone to secure the flexible strand to the second bone,
    wherein the first suture anchor has an internal passage extending longitudinally along a central axis, and the resilient member is at least partially external to the internal passage; wherein the first and second bones are pre-drilled prior to fixating the first and second suture anchors.

12. The surgical method of claim 11, wherein the resilient member is disposed partially inside the internal passage.

13. A surgical method, comprising:
    fixating a first suture anchor in a first bone, the first suture anchor having a central axis, a distal end portion, a proximal end portion, an internal passage extending longitudinally along the central axis between the distal end portion and the proximal end portion to define an anchor body, a resilient member at least partially external to the internal passage, and a flexible strand attached to the resilient member;
    passing the flexible strand from the first suture anchor through a portion of a second suture anchor;
    tensioning the flexible strand; and
    fixating the second suture anchor in a second bone to secure the flexible strand to the second bone; wherein the first and second bones are pre-drilled prior to fixating the first and second suture anchors.

14. The surgical method of claim 13, wherein the tensioning of the flexible strand compresses the resilient member.

15. The surgical method of claim 13, wherein the first and second bones are bones in a shoulder, knee, or ankle joint.

16. The surgical method of claim 13, wherein the second suture anchor is configured differently than the first suture anchor.

17. The surgical method of claim 13, wherein the second suture anchor is a knotless anchor.

18. The surgical method of claim 13, wherein the resilient member is a tapered wedge and wherein the tapered wedge has a flared portion at a distal end.

19. The surgical method of claim 13, wherein the suture anchor is a spring loaded suture anchor and the second suture anchor is a non-spring loaded suture anchor.

* * * * *